United States Patent [19]

Jones, Jr. et al.

[11] Patent Number: 4,706,685

[45] Date of Patent: Nov. 17, 1987

[54] SPIROMETER WITH DOUBLE ROLLING SEALS

[76] Inventors: William C. Jones, Jr.; William C. Jones, both of 143 Briarwood North, Oak Brook, Ill. 60521

[21] Appl. No.: 907,318

[22] Filed: Sep. 15, 1986

[51] Int. Cl.$^4$ .............................................. A61B 5/08
[52] U.S. Cl. .................................... 128/725; 128/727; 73/263
[58] Field of Search ..................... 128/725, 727, 728; 92/83; 73/262, 263, 269

[56] References Cited

U.S. PATENT DOCUMENTS

| | | | |
|---|---|---|---|
| 3,086,515 | 4/1963 | Jones | 128/728 |
| 3,722,506 | 3/1973 | McMillan, Jr. | 128/727 |

FOREIGN PATENT DOCUMENTS 489502  2/1976  U.S.S.R. ............................. 128/728

*Primary Examiner*—William E. Kamm
*Assistant Examiner*—Randy Citrin
*Attorney, Agent, or Firm*—Tilton, Fallon, Lungmus

[57] ABSTRACT

A spirometer having double rolling seals, each seal comprising an annular elastomeric membrane folded upon itself and arranged between a piston and a cylindrical casing so that the rounded folds of the two membranes face each other. When the piston is fully extended, a major portion of the axial length of one of the membranes extends axially well beyond the rear limits of the piston; however, that membrane is nevertheless retained alongside the inner surface of the casing, and does not collapse inwardly into the path of return movement of the piston, because of a protective effect provided by the second membrane. Additional assurance against inward collapse may be achieved by depressurizing the annular space between the opposing membranes. A serpentine leaf spring returns the piston to its zero position and is configured and arranged to provide diminishing resistance with increasing forward travel of the piston.

17 Claims, 7 Drawing Figures

FIG. 1A PRIOR ART (HYPOTHETICAL)

FIG. 1B PRIOR ART (HYPOTHETICAL)

SPIROMETER WITH DOUBLE ROLLING SEALS

BACKGROUND AND SUMMARY

U.S. Pat. No. 3,722,506 discloses a spirometer in which a seal is formed between the piston and the inner surface of the cylinder by a rolling seal membrane interposed between the two members. A similar construction, illustrative of the prior art, is shown herein in FIG. 1. The spirometer, intended for measuring the breathing volume or breathing rate of human subjects, includes a cylindrical outer casing 10 having a tubular inlet 11 at one end for the entry (and discharge) of expired air. Air entering the cylindrical casing displaces piston 12 towards the forwardly-extended position shown in the drawing, and the extent of displacement is recorded by suitable recording means 13 connected to piston shaft 14. A U-shaped sealing membrane 15 is interposed between the outer surface of the piston and the inner surface of the cylindrical casing with one edge 15a of the membrane being sealed to the piston and the other edge 15b being sealed to the casing.

FIG. 1 shows the piston at or near maximum extension although, if it were not for rear end wall 16 that acts as a stop, the piston would be free to travel additional distance forwardly until membrane 15 became stretched along the inside wall of the casing as shown hypothetically in FIG. 2. In such a hypothetical situation, the stroke and volume of the spirometer would be increased, resulting in a spirometer of greater capacity for any given diameter. However, such an extended-stroke spirometer is not known in the prior art. An important reason is believed to lie in the fact that if the piston stroke were extended as shown in FIG. 1A, the membrane would no longer be supported by the piston and would be free to collapse into the chamber as shown in hypothetical FIG. 1B. The possibilities of such collapse would be increased should ambient pressure exceed the pressure within the chamber. Thus, should internal pressure drop off at the end of a forceful discharge of expired air into the chamber, ambient pressure on the opposite side of the membrane would exert a force in the direction of arrow 17, causing the membrane 15 to collapse or bulge into the chamber and interfere with return movement of the piston (FIG. 1B).

One aspect of this invention lies in recognizing and understanding the problem described above and the functional reasons for it; another aspect lies in the discovery that such problem may be overcome by an uncomplicated and highly effective arrangement of two rolling membranes disposed so that one acts as a buffer to protect the other against pressures that would otherwise promote membrane collapse. The result is a spirometer of expanded stroke and volume for a given diameter or, conversely, a unit of smaller diameter, with lower inertia and greater sensitivity, for a given volumetric capacity.

The reversely-folded elastomeric membranes have their respective edges secured to the outer surface of the piston and the inner surface of the cylinder so that the rounded folds of the membranes face each other. A limited space is provided between the external surfaces of the folds, and means may be provided for reducing pressure in that space to insure against the possibility of membrane collapse and to improve the rolling action of the membranes as the piston extends and retracts. Since the provision of reduced pressure within the inter-membrane space tends to cause a slight stretching and an increase in roundness of curvature of the membranes in the area of the folds, greater linearity of response tends to result. Stated differently, initial resistance to piston movement that might otherwise be caused by sharpness or abruptness of the folds, and by the forces necessary to alter their configuration, is reduced because the lower pressure in the inter-membrane space causes a slight stretching and enlarging of the folds and gives them a smoother and more uniformly rounded contour which in turn produces a more effective low-resistance rolling action of the sealing members or membranes.

The double rolling seal of this invention not only permits greater piston stroke and spirometer capacity for a given piston diameter, but also produces smoother and more uniform rolling sealing action, enhances linearity of response, and promotes self-alignment of the piston. Return of the piston to its starting or "zero" position is effectively achieved by a serpentine leaf spring connected to the piston and the spirometer housing. The spring, although similar in appearance to the leaf spring disclosed in U.S. Pat. No. 3,086,515, is mounted and arranged to perform a different function and achieve a different result. Specifically, the serpentine spring as used herein is arranged so that its piston-returning force is at its greatest when the piston is fully retracted (i.e., in its zero position) and progressively diminishes as the piston is extended. When the piston reaches the forward limit of its travel, the spring is close to a neutral condition with the return force exerted by the spring being at a minimum for the spirometer system.

Other features, objects, and advantages of the invention will become apparent from the specification and drawings.

DRAWINGS

FIG. 1A and 1B are cross sectional views of a hypothetical modification of the structure shown in FIG. 1, such views schematically depicting a problem that would arise if such modification were made.

DETAILED DESCRIPTION OF PREFERRED EMBODIMENT

Figure 3:
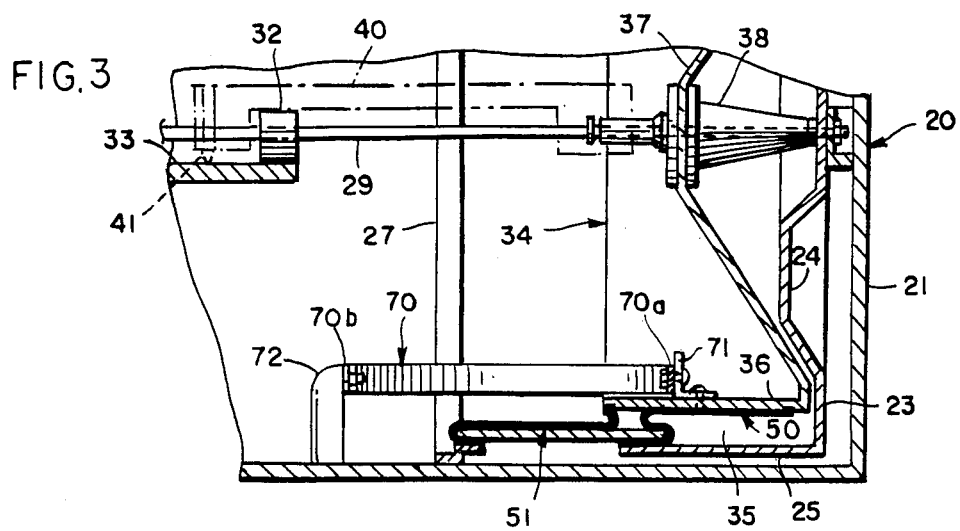
FIG. 3 is a fragmentary vertical view taken along line 3—3 of FIG. 2.
Figure 4:
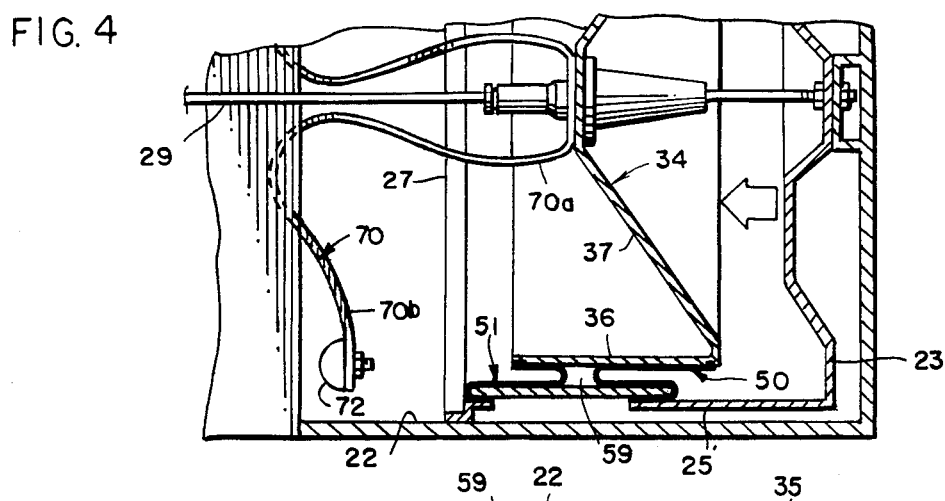
FIG. 4 is a fragmentary horizontal sectional view similar to FIG. 2 but showing the piston in an intermediate position.
Figure 5:
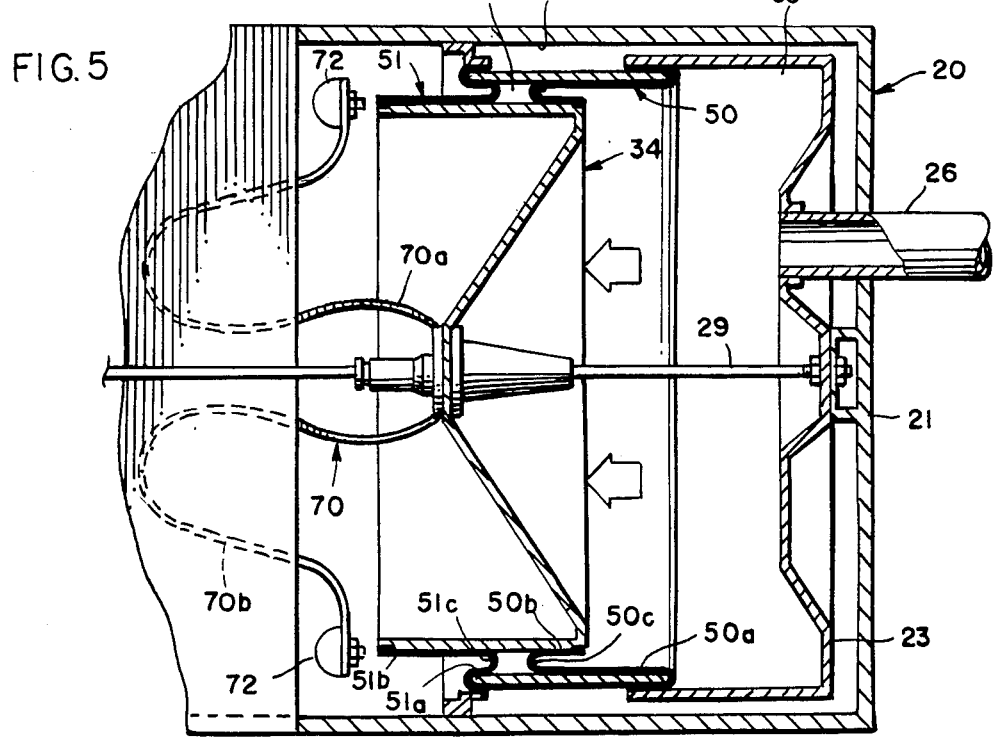
FIG. 5 is a sectional view similar to FIG. 2 but showing the piston in its fully extended or forward position.

Referring to FIGS. 3–5 of the drawings, the numeral 20 generally designates a spirometer having a housing 21 defining a chamber 22 in which is mounted a generally cylindrical casing 23. The cylindrical casing is supported with its axis extending horizontally. One end of the cylindrical casing is open; the opposite end is closed by end wall 24 except for a breathing tube 26 that extends through both the end wall 24 and the spirometer housing 21. In the illustration given, the cylindrical side wall 25 is formed in two sections, a front section 25a and a rear section 25b, but it is to be understood that the two-section construction is advantageous primarily for ease of manufacturing and servicing and that, if desired, the outer casing 23 may be formed as a single unitary structure.

Figure 1:
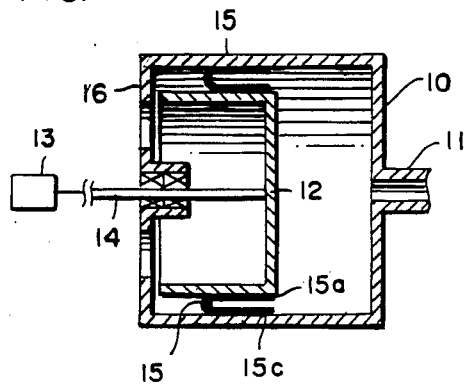
FIG. 1 is a cross sectional view of a spirometer having a rolling seal of a type previously known, such view intended to be illustrative of the prior art and being so labeled.
Figure 2:
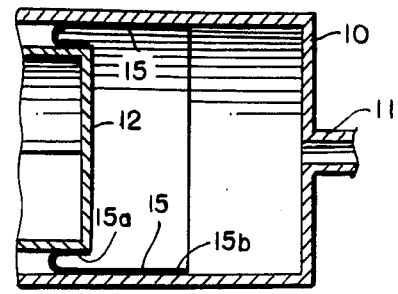
FIG. 2 is a fragmentary horizontal sectional view of a spirometer embodying this invention, the piston of the unit being shown in its retracted or zero position.
Figure 2:
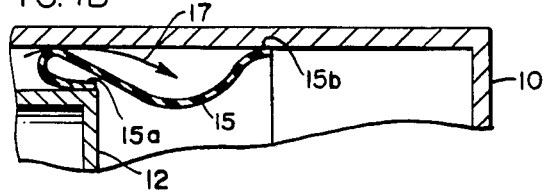
Figure 2:
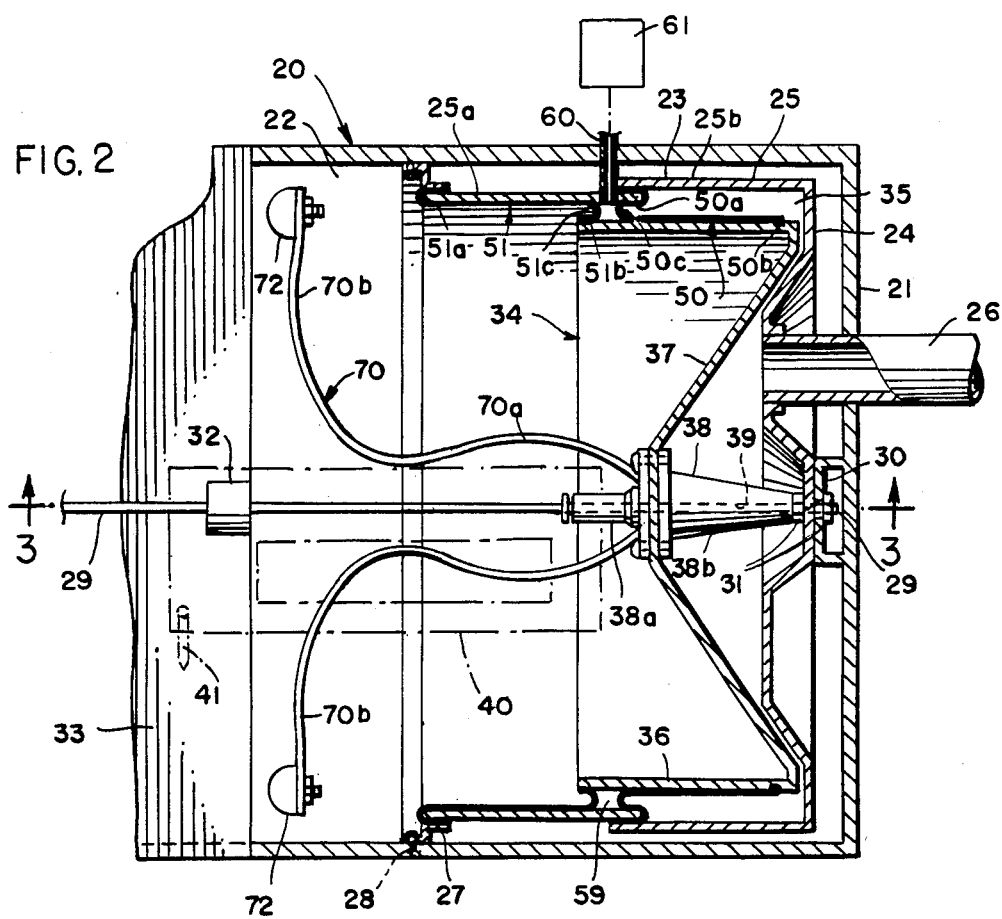

The outer casing 23 is supported within chamber 22 partly by means of an annular collar 27 which fits tightly about the open end of the casing and which may be secured by screws 28, or by any other suitable means, to the wall of housing 21. Also, in the construction illustrated in the drawings, the casing 23 is supported within chamber 22 by a horizontal guide rod 29 which extends axially through the casing and has its threaded end 29a projecting through end wall 24 at a central point and through apertured mounting bracket 30 of housing 21. Nuts 31 securely anchor one end of the guide rod in place. As shown in FIGS. 2 and 3, the guide rod has its forward end portion projecting through a second mounting bracket 32 carried by platform 33 of the housing.

A generally cup-shaped piston 34 is disposed within the cylindrical chamber 35 of the outer casing 23, the piston having a cylindrical side wall 36 and a conical concave end wall 37. An elongated hub 38, composed of a front section 38a and a rear section 38b, is secured to end wall 37. A bore 39 extends through the hub, and through that portion of the end wall 37 sealed between the two sections of the hub, and slidably receives the horizontal guide rod 29.

The piston 34 is operatively connected to suitable recording or indicating means for registering the extent of piston travel as expired air is forced into (and in some cases withdrawn from) breathing tube 26. In the illustration given, a horizontal arm 40, shown only in phantom, is journaled on guide rod 29 and is connected to hub 38 so that as the piston extends and retracts the arm will also travel forwardly and rearwardly. The arm carries a stylus 41 for registering movement of the piston on a graph sheet carried by a moving platen or rotating drum (not shown). Since such measuring or recording means are well known in the art, and since the details thereof constitute no part of this invention, further discussion is believed unnecessary. It is to be understood, however, that such measuring means may take the form of a potentiometer and, in that event, movement of the piston would be represented and recorded by associated electronic means, including a digital display, all as well known in the art.

It will be observed that the outside diameter of the cylindrical piston 34 is substantially smaller than the inside diameter of the outer casing 23, and that the axial length of the piston is also substantially less than the length of the chamber 35 defined by that casing. Specifically, chamber 35 has a length roughly twice the length of piston 34. More significantly, when piston 34 is fully extended as shown in FIG. 5 — that is, when it is shifted forwardly (to the left) as far as possible—the effective portion of the chamber 35 between the closed end of the piston and the end wall 24 of the casing has an axial length substantially greater than the length of the piston, in contrast to prior systems in which such effective length seldom (if ever) has been sufficient even to equal piston length.

In the annular zone between the inner surface of cylindrical casing side wall 25 and the concentric outer surface of piston side wall 36 are a pair of annular membranes 50 and 51 each formed of elastomeric material. Each membrane may be regarded as being generally cylindrical in shape when in an unfolded and untensioned state although, as described in U.S. Pat. No. 3,722,506, the actual shape may be slightly frusto conical with the outer end portions 50a and 51a being slightly larger in diameter than inner end portions 50b and 41b.

Membrane 50 is reversely folded upon itself with its annular folded portion 50c disposed within the axial limits of piston 34 (regardless of the position of that piston), with its outer annular end portion 50a sealingly secured to the inner side wall of casing 23 and with its inner annular end portion 50b sealingly secured to the piston adjacent its front end. By forming the outer casing 23 in two sections, the extreme rear end of the membrane 50 may be tightly clamped between the side walls of the two sections with the membrane additionally serving as a sealing gasket between those sections. A suitable adhesive or sealant may be used to secure the extreme rear end 50b of the membrane to the side wall 36 of the piston as schematically represented by the slightly increased thickness of that portion of the membrane; alternatively, clamping means in the form of an external band may be extended about the extreme rear end of portion 50b for the purpose of maintaining an air tight seal between the membrane and the piston.

The axial length of membrane 50 when the piston is either fully retracted (FIG. 2) or fully extended (FIG. 5) is only slightly less than the length of the piston itself. Also, the front end portion 50a of membrane 50 is secured to the casing wall 25 at a distance from end wall 24 that approaches the axial length of piston 34. Thus, the distance of piston travel from its retracted position to its fully extended position substantially exceeds the axial length of the piston.

The second membrane 51 is secured to the casing and the piston in opposing relation with respect to membrane 50. Specifically, membrane 51 is also reversely folded upon itself and its outer annular end portion 51a is sealingly secured to the side wall 25 of the casing. In the illustration given, end portion 51a is rolled over the edge of the casing's open end and is tightly and sealingly clamped between the casing 23 and annular collar 27. The membrane's inner annular end portion 51b is sealingly secured to piston 34 adjacent the front end of that piston. Again, suitable adhesives or clamping means (in the form of an encircling strap or band) may be provided to hold the extreme end of the reversely-turned end portion 51b in place against the outer front end of the piston.

The two membranes have their folded portions 50c and 51c facing each in opposing relation. Although the location of each fold changes for a given membrane as the membranes roll during piston extension and retraction, the relationship of the rounded annular fold of one membrane with respect to the opposing fold of the other membrane remains constant regardless of piston location.

The membrane should be mounted so that their folds are disposed axially apart to define an annular space 59 therebetween. Such an arrangement avoids friction that would otherwise be generated by contact between the membranes. In addition, the spacing of the folds has a stabilizing effect on the piston, thereby reducing stresses that might increase friction between the piston and its guide rod 29.

The side wall 25 of the cylindrical casing 23 may be provided with one or more apertures connected to an evacuation line 60 leading to a suitable pump 61 or other vacuum source capable of developing a mild relative vacuum (approximately 1 to 10 centimeters of water) within the space 59 between membranes 50 and 51. Because of such a relative vacuum, atmospheric pressure exerts a force on both walls of the elastomeric membranes, keeping them affixed but still movable as necessary. It has been found that such a relative vacuum also reduces any adverse effects of the pressure differential between ambient pressure and the pressure within the forward portion of chamber 35. The vacuum produces a slight stretching of the elastomeric membranes and causes them to develop a smoother and more uniform roundness in the areas of the folds. This helps to eliminate any initial non-linearity of response whenever the piston changes direction. In general, the relatively positive external pressure gives the annular membrane seals an even smoother and more effective rolling action about the periphery of the piston 34 as the piston travels forwardly and rearwardly.

The membranes 50 and 51 may be formed of any durable, non-pervious, highly-deformable elastomeric material. Silicone rubber has been found particularly effective, but other materials having similar properties may be used.

A contoured symmetrical leaf spring 70 is connected at its midpoint to piston 34 by means of bracket 71 (FIG. 3) and has its ends secured to spaced projections 72 within the chamber 22 of housing 21. The projections 72 are preferably equidistant from the central axis of piston 34 (i.e., from guide rod 29) and are located beyond the forward limit of travel of the piston (FIG. 5).

The central portion 70a of the spring is bowed rearwardly regardless of the position of piston 34 (compare FIGS. 2, 4, 5) but the lateral arm portions 70b assume different configurations depending on the position of the piston. With the piston fully retracted, the arm portions 70b project laterally outwardly in opposite directions and in generally the same plane (FIGS. 2, 3). As the piston advances, arm portions 70b develop a forwardly-directed curvature until, at the point of maximum forward travel of the piston, the bowed configuration of each arm portion 70b appears as a reverse image, and of almost equal size, as the bowed central portion 70a of the spring (FIG. 5). In the condition shown in FIG. 5, spring 70 has almost reached a neutral condition; if the piston were capable of appreciably additional forward movement without obstruction from projections 72 or other suitable stop means, the action of spring 70 would be reversed and the spring would exert a forward pulling force on the piston. Since the piston is incapable of substantial further forward movement, spring 70 always exerts a rearward or return force on the piston; however, that force varies depending on the location of the piston with such force being at a minimum when the piston is fully extended (FIG. 5) and at a maximum when it is fully retracted (FIG. 2). The result is that the spring effectively urges the piston into its fully retracted or zero position but provides no appreciable resistance to forward movement of the piston during the latter portion of its forward travel when the rate of expired air flowing into chamber 35 is relatively low. The greater resistance imposed by the spring at the commencement of piston advancement does not adversely affect operation of the instrument because at the commencement of a test the force and flow rate of expired air entering the spirometer are at maximum levels.

In the operation of the spirometer as, for example, in a forced expiratory volume (FEV) test, a patient exhales into a suitable mouthpiece (not shown) connected to breathing tube 26 with piston 34 initially in the retracted position shown in FIG. 2. Under those conditions, a major portion of the axial length of the second membrane 51 extends rearwardly along the inner surface of casing wall 25 beyond the front of the piston. As the entry of expired air causes the piston to be advanced, the rounded fold 51c of membrane 51 migrates to the intermediate zone of that membrane until each membrane, when viewed in section, assumes a generally U-shaped configuration (FIG. 4). Continued advancement of the piston then causes membrane 50 to unroll, exposing a portion of its length along wall 25 behind piston 34. In normal operation, the piston would not reach the extreme forward limits of its stroke since that would mean that the FEV exceeds the volumetric capacity of the spirometer; however, when for any reason the piston is shifted forwardly to its maximum extent, it will be observed that the first membrane 50 has the major portion of its axial length extending rearwardly behind the piston along the inside surface of casing wall 25 (FIG. 5).

While in the foregoing, we have disclosed an embodiment of the invention in considerable detail for purposes of illustration, it will be understood by those skilled in the art that many of these details may be varied without departing from the spirit and scope of the invention.

We claim:

1. A spirometer for measuring breathing functions of human subjects, said spirometer having a cylindrical casing with rear and side walls defining a cylindrical chamber open at one end; a cylindrical piston supported for axial movement within said chamber; said piston being connected to indicating means for indicating the axial travel of said piston; port means in said rear wall for the entry and removal of expired air into and from said chamber behind said piston; and sealing means disposed between said piston and the inner surface of said casing; wherein the improvement comprises said sealing means being in the form of first and second annular membranes each formed of elastomeric material; said first membrane being reversely folded upon itself to provide an outer annular end portion sealingly secured to the inner side wall of said casing and an inner annular end portion sealingly secured to said piston adjacent the rear end thereof; said second membrane also being reversely folded upon itself to provide an outer annular end portion sealingly secured to the inner side wall of said casing and an inner annular end portion sealingly secured to said piston adjacent the front end thereof; said first and second membranes being arranged with their respective folds facing each other; said first membrane having the major portion of its axial length extending rearwardly behind said piston when said piston is at the forward limit of its stroke; and said second membrane having the major portion of its axial length extending forwardly beyond said piston when said piston is at the rearward limit of its stroke.

2. The spirometer of claim 1 in which each of said membranes is generally cylindrical when in unfolded condition.

3. The spirometer of claim 1 in which the folds of said first and second membranes are spaced apart to define, along with said casing and piston, an annular space of generally constant volume but shifting location during spirometer operation.

4. The spirometer of claim 3 in which means are provided for maintaining the pressure of said space below atmospheric pressure.

5. The spirometer of claim 4 in which the negative pressure within said space is maintained at 1 to 10 cubic centimeters of water.

6. The spirometer of claim 4 in which said side wall of said casing is provided with an outlet port communicating with said annular space; said means for maintaining the pressure of said annular space below atmospheric pressure comprising a vacuum pump connected to said outlet port.

7. The spirometer of claim 1 in which said first membrane has the major portion of one surface thereof facing outwardly towards said side wall of said casing when the piston is at the rearward limit of its stroke and facing inwardly away from said side wall when said piston is at the forward limit of its stroke.

8. The spirometer of claim 1 in which said second membrane has the major portion of one surface thereof facing outwardly towards said side wall of said casing when said piston is at the forward limit of its stroke and facing inwardly away from said side wall when said piston is at the rearward limit of its stroke.

9. A spirometer for measuring breathing functions of human subjects, said spirometer having a cylindrical casing with rear and side walls defining a cylindrical chamber open at one end; a cylindrical piston supported for axial movement within said chamber; said piston being connected to indicating means for indicating the axial travel of said piston; port means in said casing for the entry and removal of expired air into and from said chamber behind said piston; and sealing means disposed between said piston and the inner surface of said casing; wherein the improvement comprises
said sealing means being in the form of first and second annular membranes each formed of elastomeric material; said first membrane being reversely folded upon itself to provide an outer annular end portion sealingly secured to the inner side wall of said casing and an inner annular end portion sealingly secured to said piston adjacent the rear end thereof; said second membrane also being reversely folded upon itself to provide an outer annular end portion sealingly secured to the inner side wall of said casing and an inner annular end portion sealingly secured to said piston adjacent the front end thereof; said first and second membranes being arranged with their respective folds facing each other; said first membrane having the major portion of its axial length extending rearwardly beyond said piston when said piston is at the forward limit of its stroke and said second membrane having the major portion of its axial length extending forwardly beyond said piston when said piston is at the rearward limit of its stroke; and spring means engaging said piston and exerting forces urging said piston rearwardly within said chamber, the forces exerted by said spring means being greater when said piston is at the rearward limit of its stroke than at the forward limit thereof.

10. The spirometer of claim 9 in which housing means extends about and supports said casing; said spring means comprising a serpentine leaf spring having a pair of arm portions extending outwardly away from each other and secured to said housing and a bowed central portion connected to said piston.

11. The spirometer of claim 10 in which said arm portions of said spring are secured to said housing at spaced points in front of the forward limit of travel of said piston; said arm portions extending laterally outwardly away from each other when said piston is retracted and bowing forwardly when said piston is extended.

12. The spirometer of claim 9 in which each of said membranes is generally cylindrical when in unfolded condition.

13. The spirometer of claim 9 in which the folds of said first and second membranes are spaced apart to define, along with said casing and piston, an annular space of generally constant volume but shifting location during extension and retraction of said piston.

14. The spirometer of claim 13 in which means are provided for maintaining the pressure of said space below atmospheric pressure.

15. The spirometer of claim 14 in which said side wall of said casing is provided with an outlet port communicating with said annular space; said means for maintaining the pressure of said annular space below atmospheric pressure comprising a vacuum pump connected to said outlet port.

16. The spirometer of claim 9 in which said first membrane has the major portion of one surface thereof facing outwardly towards said side wall of said casing when said piston is at the rearward limit of its stroke and facing inwardly away from said side wall when said piston is at the forward limit of its stroke.

17. The spirometer of claim 9 in which said second membrane has the major portion of one surface thereof facing outwardly towards said side wall of said casing when said piston is at the forward limit of its stroke and facing inwardly away from said side wall when said piston is at the rearward limit of its stroke.

* * * * *